(12) United States Patent
Grabbe et al.

(10) Patent No.: US 10,207,236 B2
(45) Date of Patent: *Feb. 19, 2019

(54) GAS DECOMPOSITION REACTOR FEEDBACK CONTROL USING RAMAN SPECTROMETRY

(71) Applicant: SunEdison, Inc., Maryland Heights, MO (US)

(72) Inventors: Alexis Grabbe, St. Charles, MO (US); Pramatha Payra, Friendswood, MO (US)

(73) Assignee: CORNER STAR LIMITED, Hong Kong (HK)

( * ) Notice: Subject to any disclaimer, the term of this patent is extended or adjusted under 35 U.S.C. 154(b) by 153 days.

This patent is subject to a terminal disclaimer.

(21) Appl. No.: 15/044,734

(22) Filed: Feb. 16, 2016

(65) Prior Publication Data
US 2016/0158721 A1    Jun. 9, 2016

Related U.S. Application Data

(63) Continuation of application No. 13/830,514, filed on Mar. 14, 2013, now Pat. No. 9,297,765.

(51) Int. Cl.
| | |
|---|---|
| *C01B 33/027* | (2006.01) |
| *C01B 33/029* | (2006.01) |
| *B01J 8/18* | (2006.01) |
| *G01N 21/65* | (2006.01) |
| *G05D 7/00* | (2006.01) |
| *C01B 33/03* | (2006.01) |
| *B01J 19/00* | (2006.01) |

(Continued)

(52) U.S. Cl.
CPC ........... *B01J 8/1809* (2013.01); *B01J 8/1818* (2013.01); *B01J 8/1827* (2013.01);
(Continued)

(58) Field of Classification Search
CPC ............................... C01B 3/027; C01B 3/029
See application file for complete search history.

(56) References Cited

U.S. PATENT DOCUMENTS

| | | | |
|---|---|---|---|
| 4,125,643 A | 11/1978 | Reuschel et al. | |
| 4,820,587 A | 4/1989 | Gautreaux et al. | |

(Continued)

FOREIGN PATENT DOCUMENTS

| | | |
|---|---|---|
| JP | 2011-178611 A | 9/2011 |
| WO | 2010135105 A1 | 11/2010 |

OTHER PUBLICATIONS

Lipp, Elmer D. et al., On-Line Monitoring of Chlorosilane Streams by Raman Spectroscopy, Applied Spectroscopy, 1998, pp. 42-46, vol. 52, No. 1, Society of Applied Spectroscopy.

(Continued)

*Primary Examiner* — Jennifer A Leung
(74) *Attorney, Agent, or Firm* — Armstong Teasdale LLP

(57) ABSTRACT

A gas decomposition reactor for the decomposition of a gas into a mixture of solid and gaseous by-products is disclosed. The gas decomposition reactor includes a reactor vessel, a Raman spectrometer, and a processor. The reactor vessel has an inlet for receiving inlet gas and an exhaust outlet for releasing exhaust gas. The Raman spectrometer is connected with the exhaust outlet for determining a chemical conversion within the reactor chamber and generating a corresponding signal. The processor is connected with the Raman spectrometer to receive the signal from the Raman spectrometer. The processor is capable of comparing the signal with a set of values and calculating differences between the signal and the set of values. The processor is connected with the inlet to regulate a flow of the inlet gas.

14 Claims, 9 Drawing Sheets

(52) U.S. Cl.
CPC ......... *B01J 19/0033* (2013.01); *C01B 33/027* (2013.01); *C01B 33/029* (2013.01); *C01B 33/03* (2013.01); *G01N 21/65* (2013.01); *G05D 7/00* (2013.01); *B01J 2208/00539* (2013.01); *B01J 2208/00548* (2013.01); *B01J 2208/00628* (2013.01); *B01J 2208/00893* (2013.01); *B01J 2219/0022* (2013.01); *B01J 2219/00162* (2013.01); *B01J 2219/00164* (2013.01); *B01J 2219/00186* (2013.01); *B01J 2219/00198* (2013.01); *B01J 2219/00202* (2013.01); *B01J 2219/00213* (2013.01); *B01J 2219/00218* (2013.01); *B01J 2219/00231* (2013.01); *B01J 2219/00995* (2013.01)

(56) References Cited

U.S. PATENT DOCUMENTS

| | | | |
|---|---|---|---|
| 4,883,687 | A | 11/1989 | Gautreaux et al. |
| 6,479,597 | B1 | 11/2002 | Long et al. |
| 6,528,316 | B1 | 3/2003 | Gosling |
| 7,505,127 | B2 | 3/2009 | Marrow et al. |
| 9,297,765 | B2 * | 3/2016 | Grabbe .................. G01N 21/65 |
| 2004/0233425 | A1 | 11/2004 | Long et al. |
| 2005/0154129 | A1 | 7/2005 | Battiste |
| 2006/0136149 | A1 | 6/2006 | Long et al. |
| 2007/0019191 | A1 | 1/2007 | Marrow et al. |
| 2007/0042566 | A1 | 2/2007 | Seacrist et al. |
| 2008/0180661 | A1 | 7/2008 | Brown et al. |
| 2010/0280664 | A1 | 11/2010 | Kemper et al. |
| 2011/0059004 | A1 | 3/2011 | Stoecklinger |
| 2012/0070362 | A1 | 3/2012 | Harms et al. |
| 2012/0283395 | A1 | 11/2012 | Hendrickson |

OTHER PUBLICATIONS

International Search Report and Written Opinion of the International Searching Authority regarding PCT/US2014/026488 dated Jul. 23, 2014, 14 pgs.

* cited by examiner

GAS DECOMPOSITION REACTOR FEEDBACK CONTROL USING RAMAN SPECTROMETRY

CROSS REFERENCE TO RELATED APPLICATION

This application is a continuation of U.S. patent application Ser. No. 13/830,514, filed on Mar. 14, 2013, entitled "Gas Decomposition Reactor Feedback Control Using Raman Spectrometry," the entire disclosure of which is incorporated by reference herein.

FIELD

The field relates generally to gas decomposition reactors and, more specifically, to systems and methods for controlling gas decomposition reactors such as fluidized bed reactors using Raman Spectrometry on input and output gas streams.

BACKGROUND

In the conventional operation of a gas decomposition reactor such as a fluidized bed reactor that produces polysilicon, input gas containing hydrogen and a silane (any of $SiH_4$, and its halogen derivatives may be used) suspends a column of seed particles in a heated reactor. The composition and flow velocity of the gas are critical parameters and operate to keep the particles suspended without fusing to each other. Currently, the conversion efficiency of the process is determined by large scale mass balance.

The gas is reactive, which may cause decomposition to occur before the gas reaches a mass flow controller, or may cause decomposition inside the mass flow controller itself. Mass flow controllers operate on Poiseuille's principle with measurements proportional to the 4th power of the diameter of a capillary. Therefore, mass flow controllers are very sensitive to deposition or corrosion inside the capillary. Corrosive gases can damage the sensor and bring it out of calibration. This is a frequent occurrence that is well known in the semiconductor industry.

Further, calibration of mass flow controllers, typically done with $N_2$ or dry air reference whose viscosity is known, does not necessarily translate to an accurate calibration for gases whose viscosities are not well known. The only experimental data found for the viscosity of silane, in open scientific literature, is two data points measured in 1921. There is no other data to compare to see if there was an error of several percent. Therefore, flow rates cannot be assured of being translated into precise compositions. Accordingly, there exists a need for a practical gas measurement system to independently check the incoming gas composition that is sensitive to the molar gas density, can simultaneously detect hydrogen and silane, and whose relative sensitivities to the gases is extremely stable in the ratiometric sense and thereby insensitive to drift in absolute calibration.

This Background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

SUMMARY

A first aspect is a gas decomposition reactor for the decomposition of a gas into a mixture of solid and gaseous by-products. The gas decomposition reactor includes a reactor vessel, a Raman spectrometer, and a processor. The reactor vessel has an inlet for receiving inlet gas and an exhaust outlet for releasing exhaust gas. The Raman spectrometer is connected with the exhaust outlet for determining a chemical conversion within the reactor chamber and generating a corresponding signal. The processor is connected with the Raman spectrometer to receive the signal from the Raman spectrometer. The processor is capable of comparing the signal with a set of values and calculating differences between the signal and the set of values. The processor is connected with the inlet to regulate a flow of the inlet gas.

Another aspect is a gas decomposition reactor for the decomposition of a gas into a mixture of solid and gaseous by-products. The gas decomposition reactor includes a reactor vessel, a Raman spectrometer, a processor, and a pressure control system. The reactor vessel has an inlet for receiving an inlet gas and an exhaust outlet for releasing an exhaust gas. The Raman spectrometer is connected with the exhaust outlet for determining a chemical conversion within the reactor vessel and generating a corresponding signal. The processor is connected with the Raman spectrometer to receive the signal from the Raman spectrometer. The processor is capable of comparing the signal with a set of values and calculating differences between the signal and the set of values. The pressure control system is connected with the processor and the inlet gas for adjusting a flow of the inlet gas through the inlet.

Various refinements exist of the features noted in relation to the above-mentioned aspects. Further features may also be incorporated in the above-mentioned aspects as well. These refinements and additional features may exist individually or in any combination. For instance, various features discussed below in relation to any of the illustrated embodiments may be incorporated into any of the above-described aspects, alone or in any combination.

BRIEF DESCRIPTION OF THE DRAWINGS

Like reference symbols in the various drawings indicate like elements.

DETAILED DESCRIPTION

Embodiments described herein generally relate to use of a gas decomposition reactor such as a fluidized bed reactor to make high purity polysilicon, as described in U.S. Pat. Nos. 4,820,587 and 4,883,687, which are incorporated herein in their entirety. A gas decomposition reactor contains and facilitates the chemical decomposition of a substance into two or more basic components. Chemical decomposition is a separation of a chemical compound into elements or simpler compounds. The chemical compound may be supplied in the form of a gas, liquid, or solid.

The gas decomposition reactor is a vessel with an inlet for receiving the chemical compound. The chemical compound is introduced into the vessel through the inlet and then subjected to an agent for causing a catalytic decomposition reaction, electrical current for causing an electrolytic decomposition reaction, or direct heat or radiation for causing a thermal decomposition reaction. Once the chemical compound is broken down into elements or simpler compounds, these products and by-products are removed from the vessel. The products and by-products may be a mixture of solids and gases.

These embodiments also apply generally to any decomposition reactor where the gas is decomposed to a mixture of solid and gaseous by-products, such as a free space reactor, or a Siemens reactor. More specifically, embodiments described herein relate to depositing silicon via chemical vapor deposition in a fluidized bed of particles. The method described herein is not limited to this particular process or configuration of reactor, but is applicable to other types of reactors chemically related to the operation of a continuous fluidized bed reactor.

Figure 1:
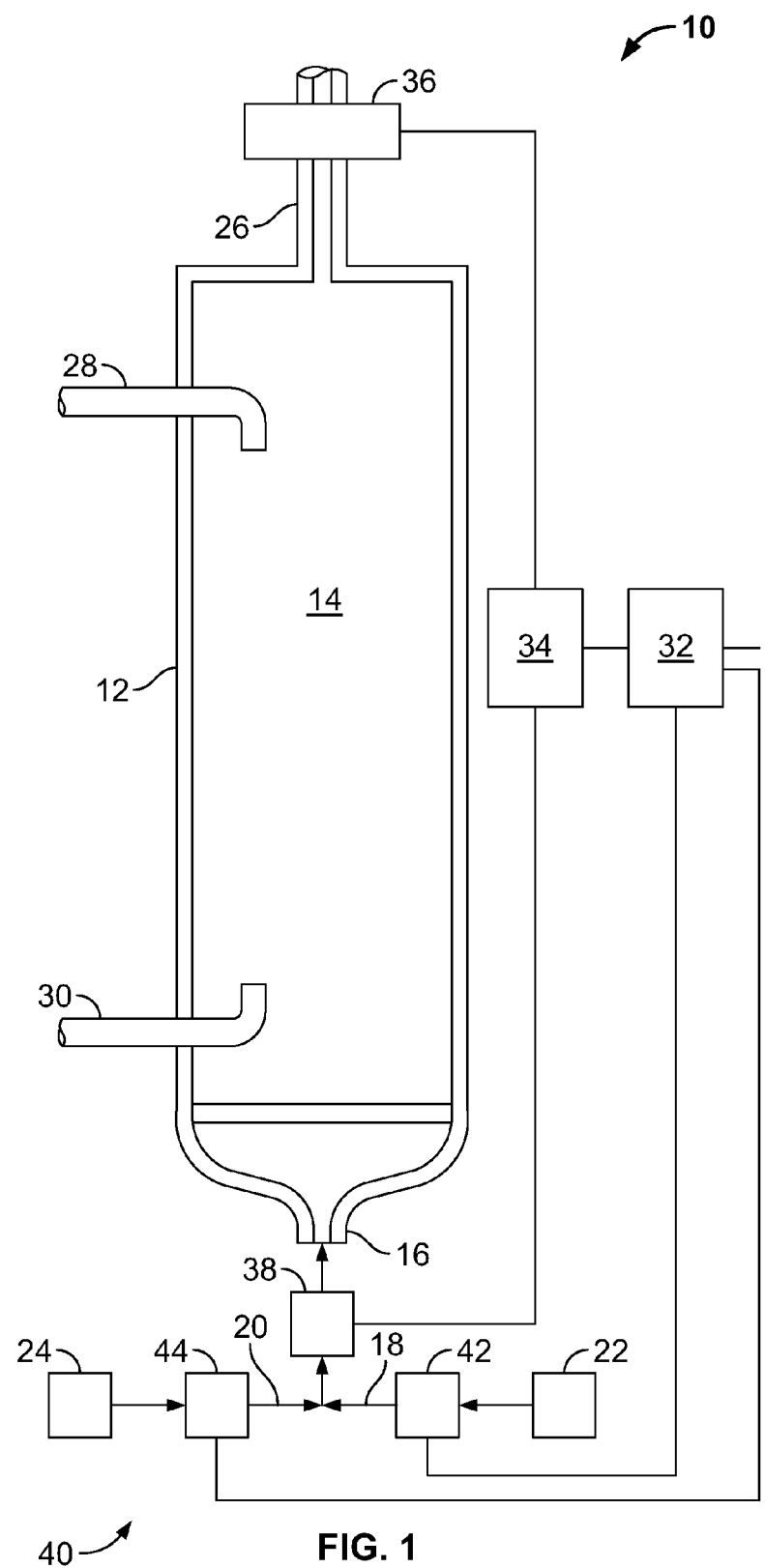
FIG. 1 is a cross-section of a fluidized bed reactor in accordance with one embodiment.

Referring to FIG. 1, a fluidized bed reactor of one embodiment is generally indicated at 10. The fluidized bed reactor 10 generally includes a reactor vessel 12 that defines a reactor chamber 14. An inlet 16 provides an inlet gas having a mixture of a reaction gas 18 or silane or first gas and a fluidizing gas 20 or hydrogen or a second gas to the reactor chamber 14. The reaction gas 18 is supplied to the inlet 16 from a reaction gas source 22 and the fluidizing gas 20 is supplied to the inlet from a fluidizing gas source 24. Off gas is exhausted through an outlet 26. The reactor chamber 14 is supplied with particles through a feeder tube 28 and larger particles/solids are removed from the reactor chamber 14 through an emptying tube 30.

The fluidized bed reactor 10 also includes a processor or feedback control system 32 connected with a Raman spectrometer 34 and a pressure-flow control system 40. The Raman spectrometer is connected with two Raman probes 36 and 38. A first Raman probe 36 is connected with the outlet 26 to determine the chemical composition of exhaust gases exiting the reactor chamber 14. A second Raman spectrometer 38 is connected with the inlet 16 to determine the chemical composition of the gas mixture entering the inlet 16. The Raman spectrometer is sensitive only to the number density of molecules in the probe and not their flow rate. Therefore, the mixture of the reaction gas 18 and the fluidizing gas 20 is measured before entering the inlet 16 so calibration drift of the probe are canceled out on measured gases. Separate measurement of the unmixed gases is prone to error due to relative drifts in calibration of different probes.

The pressure-flow control system 40 includes a reaction control valve 42 connected with the reaction gas 18 and a fluidizing control valve 44 connected with the fluidizing gas 20. The reaction gas 18 passes from the reaction gas source 22 through the reaction control valve 42 before mixing with the fluidizing gas 20 the Raman spectrometer 38 and entering and then the inlet 16. The fluidizing gas 20 passes from the fluidizing gas source 24 through the fluidizing control valve 44 before entering the Raman spectrometer 38 the inlet 16.

The processor 32 of this embodiment receives signals from the Raman probes 36 and 38, via the Raman spectrometer 34, to determine the chemical composition of the mixture of reaction gas 18 and the fluidizing gas 20, and the exhaust gas. The chemical composition of the gases is then analyzed by the processor 32.

The conversion of silane gases to silicon in fluidized bed reactors is calculated using Raman spectra taken at inlet and outlet streams. The conversion efficiency is determined by ratiometric measurements, which do not rely on gas density or viscosity. Silane, disilane, and hydrogen gases are detected simultaneously allowing feedback control of process conditions in real time. The flow rates of the reaction gas 18 and fluidizing gas 20 is adjusted using the pressure-flow control system 40.

Use of the above embodiments permit the detection of gaseous by-products, such as disilane ($Si_2H_6$) in the example if $SiH_4$ decomposition, allowing conversion efficiency to be calculated based on the existence of a di silane content. The conversion efficiency changes correlating to exhaust filter pressure drop is a transient that can be detected by the in-line measurement. Similarly, in the case of halosilane decomposition, the relevant gaseous by-products are also accounted for in the mass balance.

During operation, the fluidized bed reactor 10 is supplied with particles (not shown) introduced into chamber 14 through feed tube 28. The particles in chamber 14 are fluidized by the fluidizing gas 20 introduced through the inlet 16. As the reaction gas or silane 18 passes over the surfaces of the particles within the reaction chamber 14, silicon is deposited on the particles, which grow in size. When the particles become too large to be supported by the fluidized gas 20, the larger particles fall down and are removed from chamber 14 through emptying tube 30.

As the fluidized bed reactor 10 operates, the Raman probes 36 and 38 transmit optical signals (spectra) of the chemical composition of the gas mixture in the inlet 16 and outlet 26 to the Raman spectrometer 34. The Raman spectrometer 34 determines the chemical composition of the gases in the inlet 16 and outlet 26, and provide the processor 32 with signals representing the chemical composition of each of the gases. The processor 32 determines the efficiency of the chemical conversion within the reaction chamber 14. The processor 32 then calculates a flow rate ratio of reaction gas to fluidizing gas that would yield optimum conversion. The processor 32 communicates accordingly with the control system 40 to optimize the flow rate of the reaction gas 18 and fluidizing gas 20 by manipulation of reaction control valve 42 and/or fluidizing control valve 44. The chemical conversion efficiency is then reevaluated through a real-time feed back control loop to continuously adjust the gases being supplied to the reaction chamber 14 based on the chemical composition of the exhaust gas exiting the reaction chamber.

Figure 2:
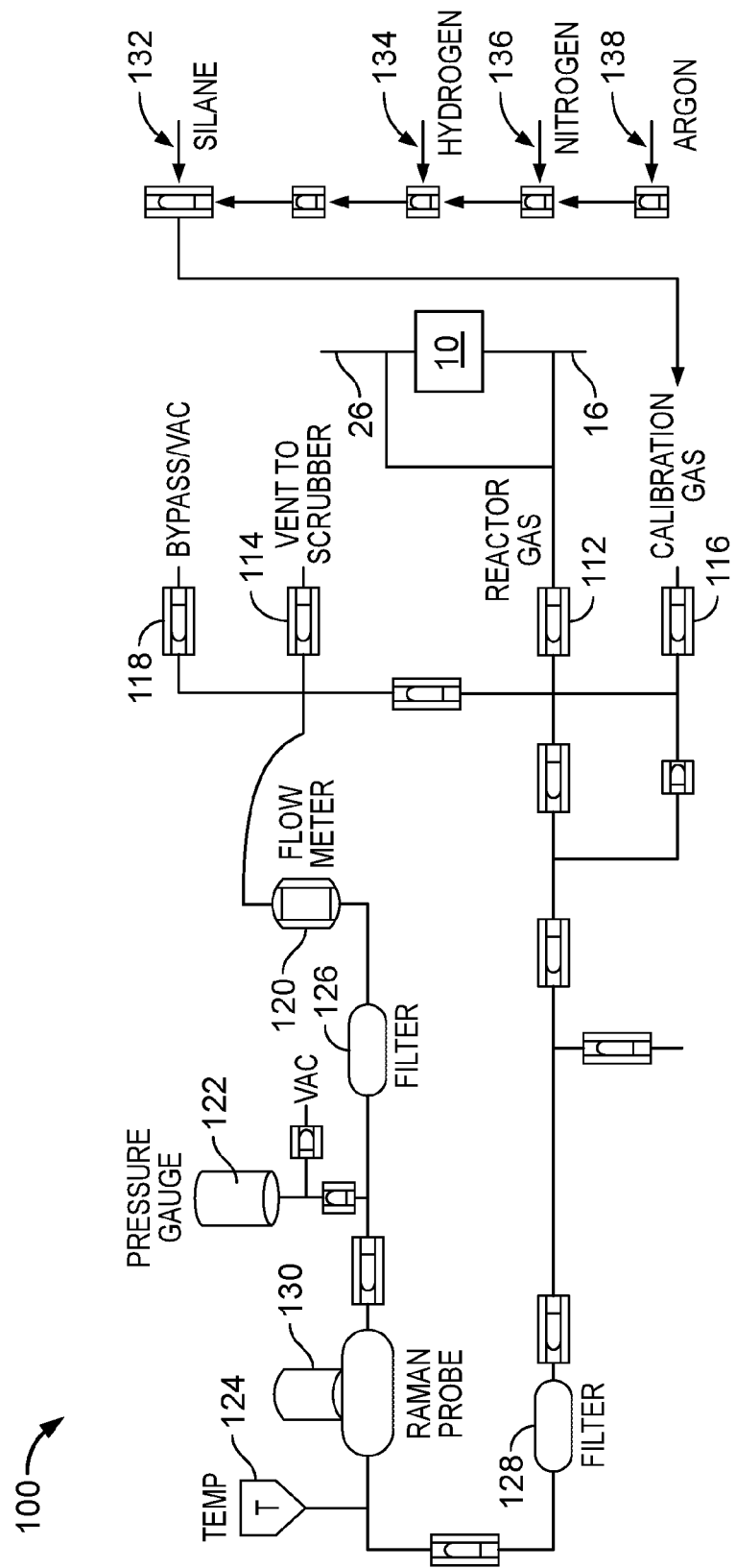
FIG. 2 is a schematic of a sampling system in accordance with another embodiment.

In another embodiment, a sampling system is shown in FIG. 2 and generally indicated at 100. The sampling system 100 is connected with the inlet 16 and outlet 26 of the fluidized bed reactor 10 through a sample inlet 112, a vent 114, a calibration gas source 116, and a bypass or vacuum 118. The sampling system 100 includes a flow meter 120, a pressure gauge 122, a thermometer 124, a pair of filters 126 and 128, and a single Raman probe 130. In this embodiment one Raman Probe is shown, but more than one Raman probe may be used.

The Raman probe 130 is used to determine the chemical composition of gases in each the inlet 16 and outlet 26 of the fluidized bed reactor 10 in sequential steps. During a first step of determining a chemical composition of an inlet gas in the inlet 16, the inlet gas first passes through a filter 128 to remove decomposed particles. The temperature of the inlet gas is then measured by the thermometer 124. Next, the chemical composition of the inlet gas is determined by the Raman probe 130. The pressure of the inlet gas within the system is then determined by the pressure gauge 122, and the flow rate is determined by the flow meter 120 before the inlet gas is evacuated from the system.

During a second step, a calibration gas is supplied from the calibration gas source 116. The calibration gas acts to both clean the sampling system 100 by removing the inlet gas and as a calibration tool. The calibration gas passes through the system in the same way as the inlet gas. However, the chemical composition of the calibration gas is known and provides a standard, or a predetermined set of values, to ensure that the sampling system 100 is maintained in a calibrated state to ensure the accuracy of the readings of the Raman probe 130.

Calibration is performed with pure gas such as silane 132, hydrogen 134, nitrogen 136, and argon 138. The pressure 122 and temperature 124 of the gas are measured with the pressure gauge 122 and thermometer 124, respectively, to determine the absolute density of the gas at the time of calibration. The gas's Raman signal at probe 130 is linearly proportional to the absolute density of the gas. The absolute reference is the pressure gauge which, is selected for linear response and precision.

During a third step, the chemical composition of an outlet gas in the outlet 26 is determined. The outlet gas travels through the sampling system 110 in the same way as the inlet gas.

Raman Spectroscopy

Currently, Raman light scattering is the only optical solution that can simultaneously detect $H_2$ and $SiH_4$. Traditionally, Raman scattering has not been used for low pressure gas applications due to poor sensitivity. However, a camera using a chilled charge coupled device (CCD) detector having quantum efficiencies on the order of 10 to 70% is used to overcome this problem. Chilled CCDs have extraordinarily low dark current (signal due to thermal fluctuations in the detector) and low read noise (spurious signals in the electronic circuitry). A Raman spectrometer with a high throughput optical system and a probe specially designed for efficient collection of scattered light can be used for low pressure gas measurements.

In gas phase measurement, the Raman signal is intrinsically linear in the number of molecules in the path of the laser beam. Unlike a Gas chromatography (GC), a Raman spectrum can be used to determine unknowns from structural information implicit in the spectra. The absolute Raman scattering factors of the gases involved must be known to design the instrumentation. These may be computed in the absence of data standards. For evaluation of equipment, absolute Raman scattering factors were computed using the theory of Georg Placzek, and the Gamess ab initio quantum chemistry code.

An expression for the signal is examined to understand why Raman spectroscopy is well suited for this application, and then a discussion is provided for how the signal is processed. A given line in watts of Raman intensity is given by the expression below. The efficiency of the detector, geometric factors, and the temperature of the gas are taken into account for instrument specific factors. If the system were not a gas system, a correction for the refractive index would be required.

$$I = \frac{1}{hv_{sig}} \frac{P_{Laser}\lambda}{hc} \left[ \frac{2^4\pi^4}{45 \cdot 3^2 c^4} \frac{h\left(\frac{c}{\lambda} - cv'_{shift}\right)^4}{cv'_{shift}\left(1 - e^{\frac{-hcv'_{shift}}{k_BT}}\right)} A_R \right] (L_e \rho N_A) C_E Q_E(v_{sig})$$

In this expression, h is Planck's constant, c is the speed of light, $\lambda$ is the wavelength of the laser, $v''_{shift}$ is the Raman shift with respect to the laser line in 1/cm, $P_{Laser}$ is the Laser power in Watts, $L_e$ is the path length of the exposed gas in the detection cell, $\rho$ is the molar density of the gas, $N_A$ is Avogadro's number, $C_E$ is the collection efficiency of the optics as a cross-section, $Q_E$ is an empirical expression for the quantum efficiency detector at the absolute wavelength of the signal, and $$v_{sig} = \frac{1}{\lambda} - v'_{shift}$$

is the absolute frequency of the Raman line. The absolute scattering factor of the molecule is $A_R$, in units of $Å^4/AMU$. The value of $A_R$ can be measured experimentally or calculated by quantum mechanical methods. The detected signal intensity in Watts divided by $hv_{sig}$ is I electron (in the CCD) counts, where $v_{sig}$ is the detected frequency of the photon.

Spectroscopy and Measurements

In a measurement of a gas composition where the signal ratios are the only interest, $v_{sig}=v_1$ and $v'_{shift}=v'_1$ for gas 1, and $v_{sig}=v_2$ and $v'_{shift}=v'_2$ for gas 2. Therefore, inserting these values into the expression for Raman intensity results in the expression for $I_1/I_2$.

$$\frac{I_1}{I_2} = \frac{\frac{1}{v_1}\left[\frac{\left(\frac{c}{\lambda} - cv'_1\right)^4}{v'_1\left(1 - e^{\frac{-hcv'_1}{k_BT}}\right)} A_1\right] Q_E(v_1)}{\frac{1}{v_2}\left[\frac{\left(\frac{c}{\lambda} - cv'_2\right)^4}{v'_2\left(1 - e^{\frac{-hcv'_2}{k_BT}}\right)} A_2\right] Q_E(v_2)} \frac{\rho_1}{\rho_2} = \frac{k_1(T)\rho_1}{k_2(T)\rho_2}$$

The ratio does not depend on the laser power, or physical characteristics of the optical cell. In mass balance calculations that only depend on the signal ratio changes in properties which change in time of the optical system, such as connection and reconnection of the optical cable or of deposition of dust on the windows or mirrors, which cancel out.

The calibration coefficients are temperature dependent, but if the temperature of calibration is the same for both gases, and the measurement of the sample is close to the calibration temperature, the temperature effect is negligible. This is equivalent to the approximation that:

$$\left(1 - e^{\frac{-hcv'_{shift}}{k_B T}}\right) \cong 1$$

This is a good approximation at room temperature. If the temperature at measurement is not allowed to vary by more than a few degrees (+/−10), the expression becomes a constant. To simplify, the value of the temperature correction is treated as 1. Thus, the following expression for signal ratios can be used:

$$\frac{I_1}{I_2} = \frac{\frac{1}{v_1}\left[\frac{\left(\frac{c}{\lambda} - cv'_1\right)^4}{v'_1} A_1\right] Q_E(v_1) \rho_1}{\frac{1}{v_2}\left[\frac{\left(\frac{c}{\lambda} - cv'_2\right)^4}{v'_2} A_2\right] Q_E(v_2) \rho_2} = \frac{k_1 \rho_1}{k_2 \rho_2}$$

Here the only error that can creep in is the long term drift of the detector response as a function of the frequency of the detected light. The short term drift is very small, and the stability has a greater relation to CCD thermal noise and read noise. However, the CCD thermal noise and read noise can be limited and controlled by chilling the detector to a constant temperature. Such modern detectors are readily available in commercial instruments. For ratiometric measurements, the Raman signals for a given set of lines inherently provide a stable response.

Data Reduction

The application to measurement of mass balance and conversion efficiency in a fluidized bed reactor will now be discussed. The example is a silane ($SiH_4$) decomposer using a hydrogen ($H_2$) fluidizing gas, although the argument can be extended to a trichlorosilane ($SiHCl_3$) decomposer, which contain hydrogen, chlorosilanes, and hydrogen chloride gases. In the equations below, the chemical notation for gas concentration [gas] in moles per liter is used, where a subscript i is the input stream, and subscript o is the output stream. Silicon solid is treated formally as mono-atomic silicon. The by-product, disilane, is included.

Even in the case of no-reaction, the measured concentrations in the inlet and outlet gas streams cannot be the same, because the local temperatures and pressures are not exactly the same. However, the mass balance to signal ratios can be coupled to determine the conversion ratios of silane to silicon, disilane and unreacted silane, and the ratio of outgoing to incoming hydrogen. Solutions that are solely in terms of signal ratios internal to each spectrum at a given probe are sought.

The signal measurement for the input gas is assumed constant between the time it is measured and the time the output signal is measured. Gas flow fluctuations on a time scale equal to or less than the measurement of gas-in and gas-out will be averaged by this method. With a single sensor and switching sample lines, stable gas flow must be maintained into the reactor for both measurements. The time scale is typically 150 seconds but can be shortened considerably. An instrument that measures simultaneously from two sample cells is immune to gas flow fluctuations, but reports average conversion for the length of time of signal collection.

Silicon balance as Si atoms: $[SiH_4]_i = [SiH_4]_o + 2[Si_2H_6]_o + [Si]_o$

Hydrogen balance as $H_2$: $[H_2]_i + 2[SiH_4]_i = [H_2]_o + 2[SiH_4]_o + 3[Si_2H_6]_o$ The mass balance is coupled to ratios of densities from Raman signals (a, b, c, d below) benefiting from cancellation of calibration drift error, as discussed above. No ratios of input to output signals (which are separate spectra) are made.

$$\frac{[SiH_4]_i}{[H_2]_i} = a\frac{[SiH_4]_o}{[H_2]_o} = b\frac{[Si_2H_5]_o}{[H_3]_o} = c\frac{[Si_3H_6]_o}{[SiH_4]_o} = \frac{c}{b} = d$$

The measurement ratio d is a dependent variable, small and relatively inaccurate, and should not be used in propagated calculations. After the algebraic manipulation below, the conversion efficiencies entirely from the measured ratios a, b, and c are discussed. Since everything is in ratios from a given spectrum, the advantage of insensitivity to detector drift can be obtained. The input and output gas streams can be measured with different Raman probe heads, with separate calibrations for each.

$$\frac{[H_2]_o}{[H_2]_i} = \frac{1+2a}{1+2b+3c} \qquad \frac{[Si]_o}{[SiH_4]_i} = \frac{(1-c)a-(b+2c)}{(1+2b+3c)a}$$

$$\frac{[SiH_4]_o}{[SiH_4]_i} = \frac{b}{a}\frac{1+2a}{1+2b+3c} \qquad \frac{[Si_2H_6]_o}{[SiH_4]_i} = \frac{c}{a}\frac{1+2a}{1+2b+3c}$$

The fractional mole conversion of input silane to output silane, output disilane, and output solids are now computed. The left hand side of the expressions is multiplied by top and bottom by $[H_2]_i$ to convert the expressions back to non-normalized density units. The expressions for conversion are expressed by the dimensionless values a, b, c which, are all ratiometric Raman derived values. Thus, once calibrated, the conversion efficiency can be steadily measured because the short and long term drift of $Q_E(v)$ is very small. The propagated error in the derived conversions is found by standard methods.

Feed Back and Control

Effective real-time measurement of a chemical conversion is made by ratiometric measurement of a gas composition using a single spectrometer. The composition of the gas stream can then be adjusted based on the measurement. The Raman system provides a check on the gas flow when the input gas composition measures differently from the feed-forward of the mass flow controllers. An incorrect gas flow can lead to de-fluidization and sintering of the fluidized bed, or wastage of the silane gas due to incomplete conversion. Additionally, excess silane input due to Mass Flow Controller (MFC) error can lead to excess formation of silicon dust.

Examples and Analysis

A silane decomposer was constructed as a fluidized bed reactor. The reactor operated by the suspended seed principle, wherein the gas flow suspends the seeds. Upon heating, the gas decomposes and deposits silicon on the seeds. Some fraction of silane decomposes and forms a dust. The dust is filtered and the spend gas is exhausted. For the purposes of this example, it does not matter if the reactor is seeded. The seeded reactors operating efficiency is dependent on tightly controlled gas composition. Feed gases to the decomposer consist of silane and hydrogen, typically with silane mole fraction with a range from 5% to 13%. The reactor used in these example runs was deliberately operated under conditions of partial conversion, from atmospheric pressure up to about 8 bar, and is referred to as the "HP-FBR."

With reference to Table 1 below, the examples discussed below are from runs labeled 67, 69, 70, 73 (at two times), and 74. The experimental input parameters are varied, but not all conditions are constant. During run 73, the pressure drop across the exhaust filter upstream of sampling changed substantially over the course of 20 minutes (FIG. 5), and the choking of the filter presumably affected sampling. The table includes processed Raman data immediately before, 73(1), and after, 73(2), this pressure drop change.

TABLE 1

Summary of calculated conversion ratio of silane to solids and disilane.

| Run | $[Si]_0/[SiH_4]_i$ | std. errors | $[Si_2H_6]_0/[SiH_4]_i$ | std. errors |
|---|---|---|---|---|
| 69 | 0.219 | 4.5E−03 | 1.69E−02 | 6.4E−05 |
| 70 | 0.291 | 4.7E−03 | 6.88E−03 | 3.1E−05 |
| 73(1) | 0.308 | 4.3E−03 | 1.01E−02 | 4.3E−05 |
| 73(2) | 0.350 | 4.1E−03 | 7.72E−03 | 3.3E−05 |
| 74 | 0.471 | 3.4E−03 | 5.00E−03 | 2.1E−05 |
| 67 | 0.493 | 3.1E−03 | 5.20E−03 | 2.1E−05 |

Analysis

Figure 3:
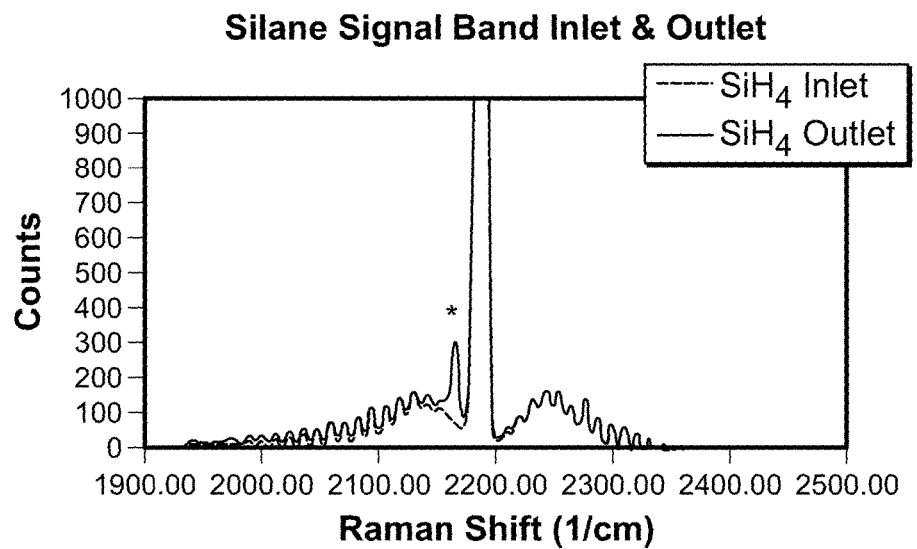
FIG. 3 is a graph plotting silane signal bands at an inlet and outlet of a fluidized bed reactor using the sampling system in accordance with FIG. 2.
Figure 4:
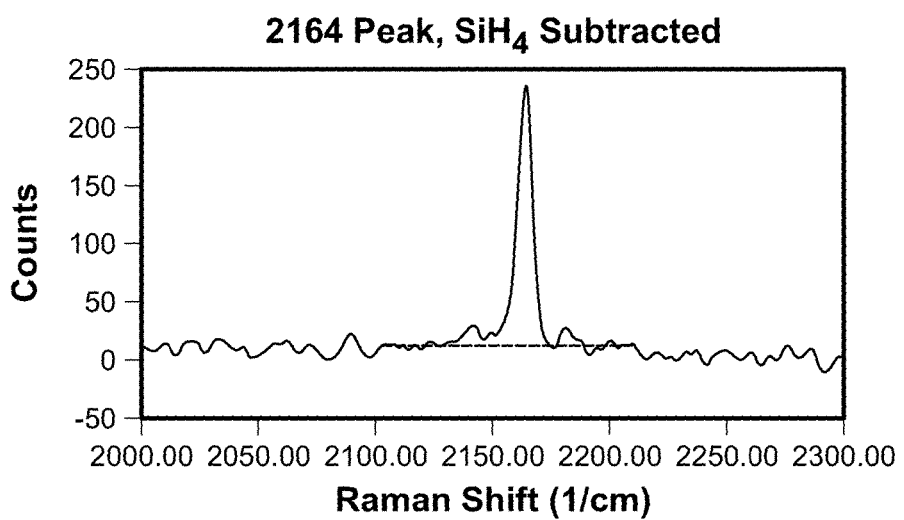
FIG. 4 is a graph plotting the 2164 peak of FIG. 3 with silane $SiH_4$ subtracted.

With reference to FIG. 3, silane Raman spectrum bands of reactor inlet and outlet gases scaled to match each other over the envelope are shown. There is an unknown peak (marked with *) at 2163.5/cm. The wings around the spectral band are rotational lines of the 2186/cm silane peak. Subtraction of $SiH_4$ reference spectrum from the outlet gas spectrum, shown in FIG. 4, reveals a sharp line with evidence of wings. The blue line is the local baseline determined by least squares analysis. (Data from run 73.)

The gas signal at 2164/cm is not silane. Suspecting that the unknown gas was a related species, an ab initio calculation of the Raman spectra of silane and disilane was undertaken. The position of the unknown peak is matched by calculation to within experimental error.

Isolating the 2164/cm peak, evidence of symmetric wings can be seen around the central line, suggesting a small molecule with low rotational inertia about at least one axis. Thus, disilane, $Si_2H_6$ is a likely candidate.

Figure 5:
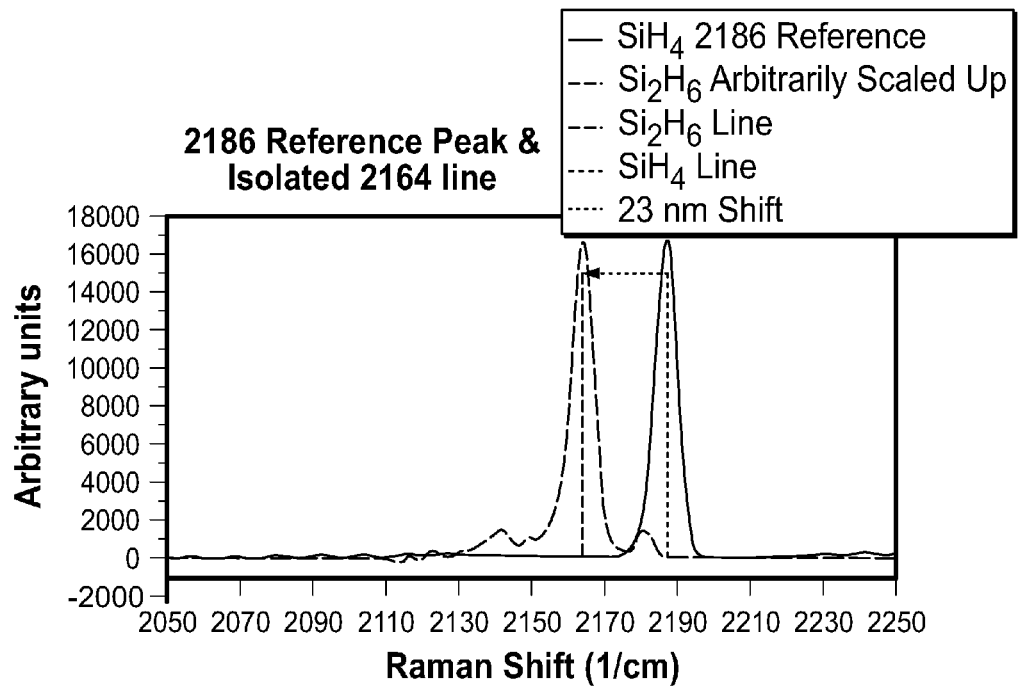
FIG. 5 is a graph plotting the 2164 peak with a 2186 reference peak.

As shown in FIG. 5, the ab initio calculated line shift of the Si—H stretch from silane to disilane matches the experimental data to within experimental error (±2/cm). The amplitudes have been scaled so the peaks have the same maximum values.

Ab initio methods for calculating line positions make certain, well known approximations. There are standard corrections to the approximations, which are known to those versed in the art and will not be discuss here. The method of calculation appropriate for computing Raman scattering factors used a diffuse correlation-consistent basis set at the MP2 level, which correlate the motions of all electrons. The calculated shift is 22/cm and the measured shift is 23/cm. However, the uncertainty in relative peak positions is at least ±1/cm and the calculation matches the data to within experimental error. Therefore, the 2164/cm peak has a high probability of being disilane.

No reference data or standards for the Raman scattering intensity of disilane known to exist. Therefore, to compute the quantity of disilane, the ratio of computed absolute scattering factors of disilane to silane was used to estimate the absolute instrumental sensitivity to calibration spectra of silane. The error in this procedure is small because the frequency shift is small, and the electronic structures are similar enough that proportional errors cancel out. Thus, the signal can be used to complete the mass balance. In addition, the quantity of disilane is relatively small. Even a large error in disilane concentration does not damage the calculation of conversion to solids. If the disilane measurement is not perfectly quantitative, the error is a proportional error. Therefore, it can still be used as an indicator of the state of the process inside the HP-FBR.

Using the calibrated measurements for silane, hydrogen, and the calculated calibration coefficient for disilane, the conversion efficiency for each of the examples is calculated. The calculated ratio of absolute Raman scattering factors is 1.78:1 $Si_2H_6$:$SiH_4$. The number and type of bond stretches are not exactly the same, and the polarizability tensors of the two molecules are not exactly the same resulting in a ratio that is not 6:4 ($Si_2H_6$ has 6 hydrogen atoms and $SiH_4$ has 4 hydrogen atoms). With this information, the conversion ratio of silane to solids and disilane can be calculated.

It should be noted, the Raman and MFC input compositions do not agree, and typically the Raman composition reads a systematically 11% higher $[SiH_4]_i/[H_2]_i$ ratio than the MFC settings. This is believed to be a calibration error, and if the Raman signal is in error it will reduce all computed conversion efficiencies by a few percent. However, this does not affect the correlations drawn from the data.

There appears to be a correlation between the disilane signal and the conversion efficiency of the HP-FBR process, provided operating conditions are similar. Further the sudden increase in conversion efficiency in run 73 corresponds to the choking of the exhaust filter. This appears to lead to longer gas residence time in a zone where silane decomposes. These observations are independent of any systematic error, as discussed above.

Runs 67 and 74 have practically the same conversion efficiency, even though conditions are different. Run 74 is hotter than run 67. However, the charge in run 67 is greater than in run 74, which, should lead to a longer dwell time in the fluidized bed. The effects of the two conditions practically cancel out.

Figure 6:
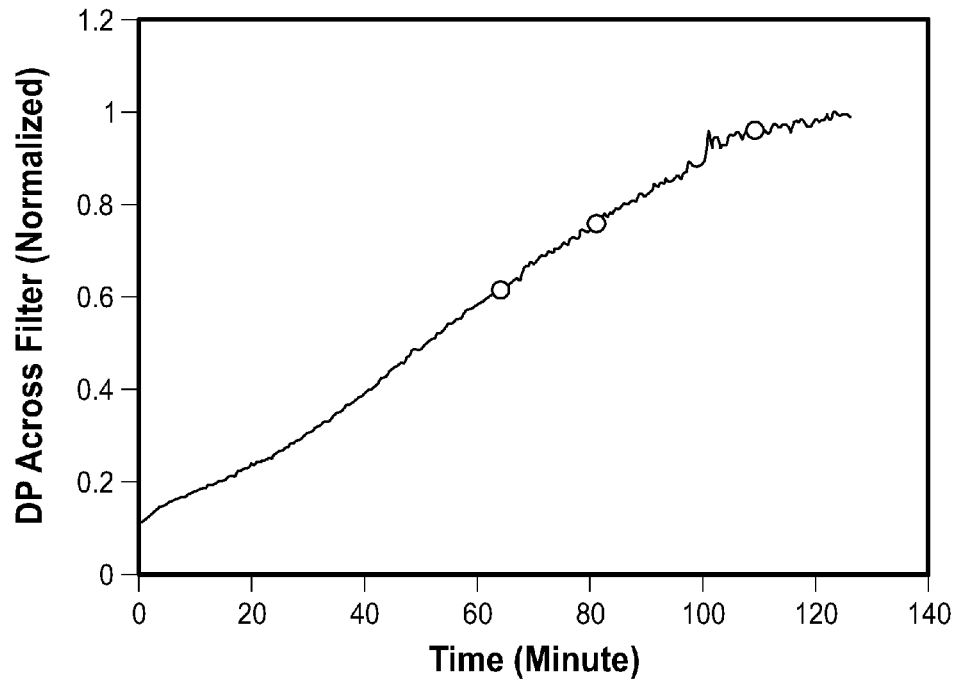
FIG. 6 is a graph plotting the pressure difference across a filter against time.

In run 73, a change in the conversion of silane to solids was detected, which brackets in time a rate change in the filter pressure, as shown in FIG. 6. The black dot marks when a Raman gas sample was taken.

Figure 7:
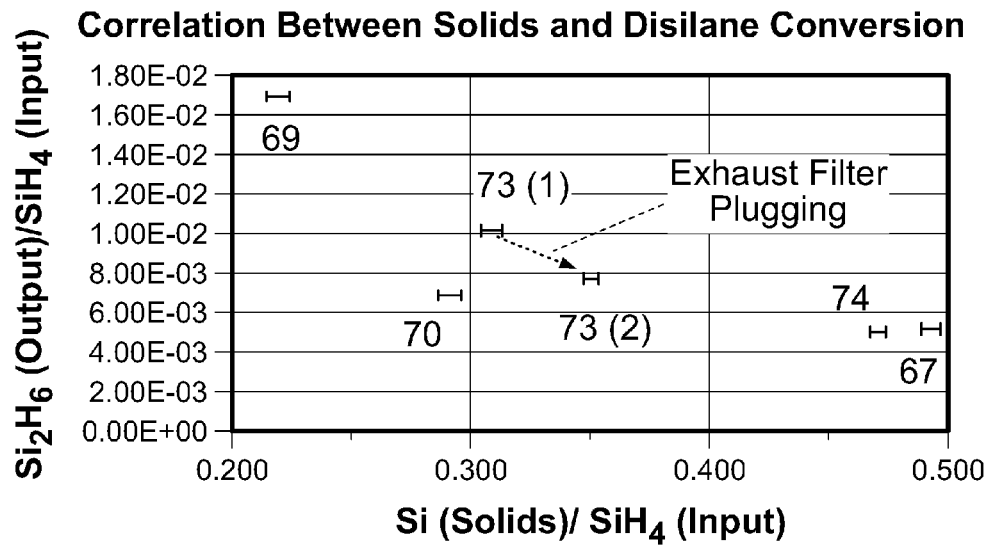
FIG. 7 is a graph plotting the correlation between solids and disilane conversion.

FIG. 7 shows the conversion to disilane signal vs. conversion to solids in molecular ratios. The sudden reduction in $Si_2H_6$ for run 73 suggests longer residence time for the gas. The measured filter pressure rose about 14.7% between the two measurements.

Appendix Raman and MFC Calibration.

Typically, the spectrometer response is calibrated at nearly room temperature, but at an elevated pressure. Therefore, the non-ideal behavior of the gas must be taken into account. The most straightforward way to correct for the non-ideal behavior of the gas is to use the Virial equation of state to second order:

$$\frac{P}{\rho RT} = 1 + B(T)\rho$$

The second virial coefficient is approximated by a function of the form:

$$B(T) = a(b - e^{c/T})$$

This is a well-documented property for hydrogen. However, there are still tables that are outrageously in error. Values taken for hydrogen (a=10.84 cm³/mole; b=2.778; c=135.55 K) are derived from a Rand technical report.

However, this is not a well-documented property for silane. There is only one primary literature reference containing PVT data on silane, by Ramaswamy and G. Gundu Rao (R&R). R&R had measured the density of oxygen in their apparatus, which allows for the correction of a systematic error in the density with modern data for oxygen using the corrected values. R&R have data for 297.71K and 193.35K, which is used to determine the Lennard-Jones parameters for the gas using the expression:

$$B(T) = N_A 2\pi\sigma^3 \int_0^\infty \left[1 - e^{-\frac{4s}{kT}\left[\left(\frac{1}{u}\right)^{12} - \left(\frac{1}{u}\right)^6\right]}\right] u^2 du$$

The R&R data, corrected by using $O_2$ gas as a reference, yields σ=4.041 Å, and ε=275.44 k.K for silane, where k is Boltzmann's constant. Based on these values, the coefficients a=328.74 cm³/mole, b=1.1974, c=167.972K are determined by application of Chapmn-Enskog theory.

The calibration errors are minimized by using an accurate pressure gauge and the virial equations of state, discussed above. A good baseline subtraction is possible during a calibration session to reduce the error to less than 0.1%.

These corrections must be made in this particular case. To calculate the density, as shown in Table 2 below, either of the following expressions may be used:

$$\rho(P, T) = \frac{P}{RT} \text{ (ideal gas approximation)}$$

$$\rho(R, T) = \frac{-RT + \sqrt{(RT)^2 + 4B(T)RTP}}{4B(T)RT} \text{ (2'd virial approximation)}$$

TABLE 2

Density of $H_2$ and $SiH_4$ gases calculated by the ideal gas law, and by the virial equation to second order. For Raman calibration at high pressures the virial equation should be used. The values in parentheses are the % error when using the ideal gas approximation.

| Gas | P = 1 Bar, 298.15K (ideal gas density) | P = 6 Bar, 298.15K (ideal gas density) | P = 1 Bar, 298.15K (virial gas density) | P = 6 Bar, 298.15K (virial gas density) |
|---|---|---|---|---|
| $H_2$ | 0.04034 (0.002) | 0.24204 (0.076) | 0.04032 | 0.24128 |
| $SiH_4$ | 0.04034 (−0.030) | 0.24204 (−1.2) | 0.04064 | 0.25389 |

The MFC data should match the Raman data for the inlet composition. There is only one primary reference available in primary literature for the viscosity of silane measured, at just two temperatures. Parameters derived from Pressure, Volume, and Temperature (PVT) data cannot be used because silane is not a true Lennard-Jones spherically symmetric molecule. As a result, the viscosity data must be reduced to determine the parameters □ and □ from fitting to a function from Chapman-Enskog theory:

$$\eta(\sigma, \varepsilon, T, m) = \frac{5}{16\sigma^2}\sqrt{\frac{mkT}{\pi}} \frac{0.9787}{\Omega(T, \varepsilon)}$$

where:

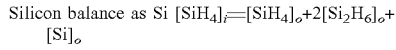

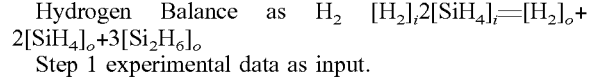

dimensionless; and m is the mass of the molecule.

The two data points from primary literature are 112.4 and 142.4 □ Poise at 15° C. and 100° C., respectively. By fitting to the viscosity formula σ=4.040Å, and ε=211.4 k.K are derived. Mass flow controllers should be calibrated to ensure a match to the above equation with these parameters. The viscosity correlates to the temperature of the gas.

The molecular radius determined from PVT and viscosity data match to 3 digits. However, the energy of the potential well (ε) does not match. This is because silane is not a perfectly spherical molecule and the resulting model deviations are different for PVT and viscosity data. Since there is no other data in the available primary literature, these are the models that are used for gas density and viscosity, but the parameters should be changed if better data becomes available. It is assumed that if after calibration, MFC data and Raman data do not match either the primary data is wrong, or the gas composition changed while flowing from the MFC to the Raman gas cell.

Figure 8:
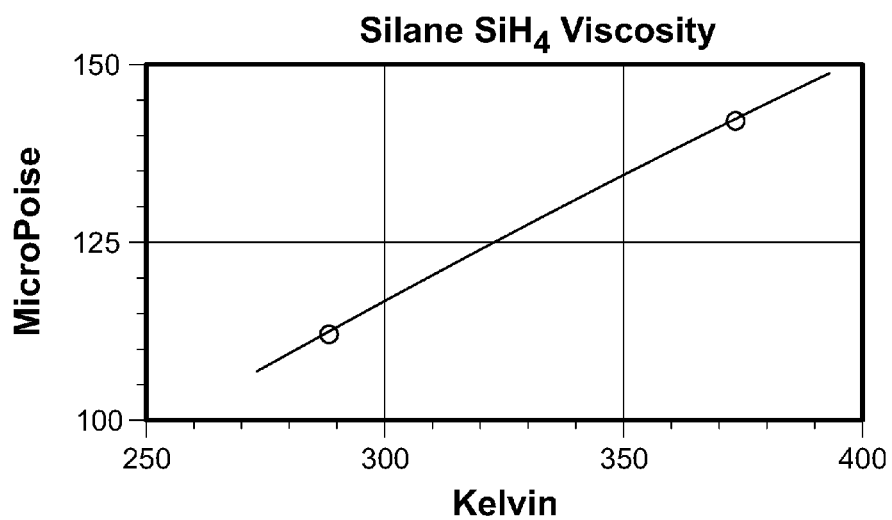
FIG. 8 is a graph plotting the viscosity of silane ($SiH_4$)

FIG. 8 shows a calculated viscosity of silane at 1.0135 Bar using the Lennard-Jones potential, Chapman-Enskog theory, and the only two published data points by Rankine.

Algebra for Data Reduction and Error Propagation.

The fractional conversion of silane can be computed strictly in terms of the ratios of signals internal to spectra, but not across sets of different spectra. The algebra used to compute fractional conversion of silane across sets of different spectra by mass balance is shown below. Similar algebra can be made for decomposition of chlorosilanes.

Step Zero Mass Balance.

Silicon balance as Si $[SiH_4]_i = [SiH_4]_o + 2[Si_2H_6]_o + [Si]_o$

Hydrogen Balance as $H_2$ $[H_2]_i 2[SiH_4]_i = [H_2]_o + 2[SiH_4]_o + 3[Si_2H_6]_o$ Step 1 experimental data as input.

$$\frac{[SiH_4]_i}{[H_2]_i} = a;$$

$$\frac{[SiH_4]_o}{[H_2]_o} = b;$$

$$\frac{[Si_2H_5]_o}{[H_3]_o} = c;$$

$$\frac{[Si_3H_6]_o}{[SiH_4]_o} = \frac{c}{b} = d$$

There are 5 constraints with 6 degrees of freedom. The ratios of the parameters can be determined by dispensing with one degree of freedom when the absolute value of all parameters are not known. Since the gas pressure/density in a gas cell is never the same as it is in the reactor this is acceptable.

Make the symbolic substitutions:

$[SiH_4]_i = w$; $[H_2]_i = u$; $[H_2]_o = v$;

$[Si]_o = x$; $[SiH_4]_o = y$; $[Si_2H_6]_o = z$.

These values may be expressed in terms of a, b and c, which are the ratios of signals inside a given spectrum:

$$X = \frac{x}{w};$$
$$Y = \frac{y}{w};$$
$$Z = \frac{z}{w};$$
$$V = \frac{v}{u}$$

Then the system of constraints becomes:

Silicon mass balance $w = y + 2z + x$

Hydrogen mass balance $u + 2w = v + 2y + 3z$

Measured Signal Ratios $a = w/u$; $b = y/v$; $c = z/v$

Step 1 Substitute the expression for w into the hydrogen mass balance, preparing to eliminate w from the system of equations.

$w = y + 2z + x$ $u + 2(y + 2z + x) - v + 2y + 3z$; $a - w/u$; $b - y/v$; $c - z/v$

Step 2 find a/b and a/c to get Y(V) and Z(V):

$a = w/u$; $a/b = (w/y)(v/u) = V/Y$; $a/c = (w/z)(v/u) = V/Z$

Step 3 Divide both mass balances by w, and list the system of equations $1 = Y + 2Z + X$ $u/w + 2(Y - 2Z + X) = v/w + 2Y + 3Z$; $a = w/u$; $Y = (b/a)V$; $Z = (c/a)V$ Step 4 Eliminate remaining w with au, express v/u as V to simplify the system of equations. The term w no longer appears.

$1 = Y + 2Z + X$ $1/a + 2(Y + 2Z + X) = V/a + 2Y + 3Z$; $Y = (b/a)V$; $Z = (c/a)V$

Step 5, with 4 equations expressed cleanly in 4 unknowns V, X, Y, Z is determined as functions of a, b, and c.

$$V = \frac{[H_2]_o}{[H_2]_i} = \frac{1+2a}{(3c+2b+1)} \qquad X = \frac{[Si]_o}{[SiH_4]_i} = \frac{1}{a}\frac{(1-c)a-(b+2c)}{(3c+2b+1)}$$

$$Y = \frac{[SiH_4]_o}{[SiH_4]_i} = \frac{b}{a}\frac{1+2a}{(3c+2b+1)} \qquad Z = \frac{[Si_2H_6]_o}{[SiH_4]_i} = \frac{c}{a}\frac{1+2a}{(3c+2b+1)}$$

The fractional conversion of silane to disilane is $Z/2$.

Error Propagation.

Variances may be found by the standard rules for error propagation for an arbitrary function $f(a,b,c)$, and the chain rule for differentiation. The square of the variance of f is given by:

$$\sigma_f^2 = \left(\frac{df}{da}\right)^2 \sigma_a^2 + \left(\frac{df}{db}\right)^2 \sigma_b^2 + \left(\frac{df}{dc}\right)^2 \sigma_c^2$$

For brevity the results are stated in a form convenient for coding.

$$\sigma_V^2 = \left(\frac{2}{(3c+2b+1)}\right)^2 \sigma_a^2 + \left(\frac{2(2a+1)}{(3c+2b+1)^2}\right)^2 \sigma_b^2 + \left(\frac{3(2a+1)}{(3c+2b+1)^2}\right)^2 \sigma_c^2$$

$$\sigma_X^2 = \left(\frac{2+b}{a^2(3c+2b+1)}\right)^2 \sigma_a^2 + \left(\frac{(c-1)(2a+1)}{a(3c+2b+1)^2}\right)^2 \sigma_b^2 + \left(\frac{(b+2)(2a+1)}{a(3c+2b+1)^2}\right)^2 \sigma_c^2$$

$$\sigma_Y^2 = \left(\frac{b}{a^2(3c+2b+1)}\right)^2 \sigma_a^2 +$$
$$\left(\frac{(3c+1)(2a+1)}{a(3c+2b+1)^2}\right)^2 \sigma_b^2 + \left(\frac{3b(2a+1)}{a(3c+2b+1)^2}\right)^2 \sigma_c^2$$

$$\sigma_Z^2 = \left(\frac{c}{a^2(3c+2b+1)}\right)^2 \sigma_a^2 + \left(\frac{2c(2a+1)}{a(3c+2b+1)^2}\right)^2 \sigma_b^2 +$$
$$\left(\frac{(1+2b)(2a+1)}{a(3c+2b+1)^2}\right)^2 \sigma_c^2$$

Intrinsic Signal Noise and Resulting Error.

The Raman signal has four significant sources of noise. Actual noise values vary from instrument to instrument, the details and values shown herein are examples from one specific instrument. First, the read noise of the detector is 7 counts per read per CCD channel. Second, the dark noise of the detector is 0.03 electrons per second per CCD pixel. A channel of one wave length is the sum of a strip of pixels. In the camera used, the spectra are split into two and stacked on top of each other across the detector surface. The instrument is the equivalent of an echelle spectrograh with a cross dispersing prism. In a given channel (wave number) the signal is integrated over ~100 CCDs. Third, the noise of a Raman signal is equal to the square root of the total number of counts. Fourth, a back-ground fluorescence due to the optical system, primarily the windows and the mirror, is a broad background except for a few lines. The fluorescence is bleached by the laser beam after a "warm-up" period, but is not entirely eliminated.

In a typical measurement, the instrument is alternated between laser on and off cycles, so the operator sees a spectrum with the read-signal and dark signal subtracted off. However, noise from those sources is still included as part of the data and must be considered. The resulting read noise and dark noise are the square root of the signals.

The variance of the dark and read noise is now determined. These two contributions are a function of the camera and temperature of the camera. However, when the temperature is chilled and held constant, its effect is negligible and can be neglected. The dark noise is strictly proportional to time and the read noise is strictly proportional to number of accumulations, provided that detector does not become saturated. Therefore, these errors grow at different rates, as discussed below.

Figure 9:
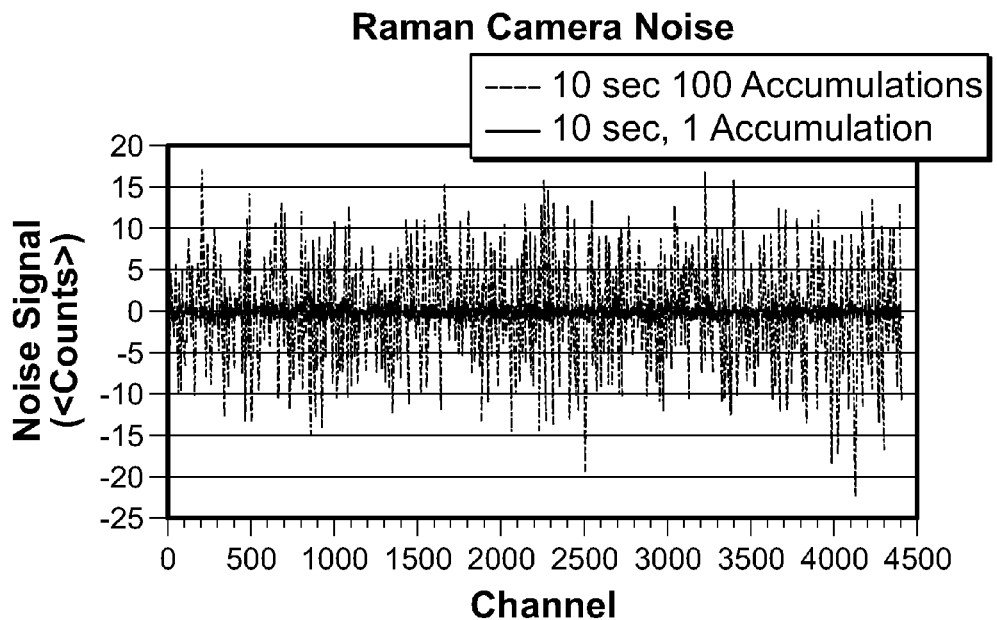
FIG. 9 is a graph plotting Raman camera noise.

Raman camera noise, shown in FIG. 9, from the Raman system with the laser turned off. There is no contribution from fluorescence. Noise is minimized by using the longest integration time possible without detector saturation, and the fewest possible accumulations. This is achieved by keeping the peak signal at ~33000 to ~53000 counts in any channel to minimize possibility of camera "blooming."

The dark signal magnitude is proportional to time, and dark noise is proportional to the square root of counts, and therefore, to square root of time. The instrument measures a signal, then turns off the laser to measure the dark signal and subtract it off. Thus, the average signal is zero, but the noise does not equal zero.

This is the signal invisible to the user, and its noise:

$$S_D = k'_d t \quad \sigma'_D = \sqrt{k'_d t}$$

The signal visible to the user is zero, but the noise from subtracting one dark signal from another is of the form:

$$\sigma_D^2 = \left(\frac{dS_D(1)}{dt}\right)^2 \sigma_D'^2 + \left(\frac{dS_d(2)}{dt}\right)^2 \sigma_D'^2 = 2k'_d \sigma_D'^2$$

Therefore, the instrumental dark noise in a channel is proportional to square root of time:

$$\sigma_D = \sqrt{k_D t}$$

The read signal is treated the same way, it should subtract out to zero. With n accumulations, the total noise is then:

$$\sigma = \sqrt{\sum_n \sigma_R^2 + k_D t}$$

For 10 seconds of signal integration, and 1 accumulation the experimental standard deviation is:

$$\sigma = \sqrt{\sigma_R^2 + k_D 10} = 0.573$$

For 1 second of signal integration, and 10 accumulation the experimental standard deviation is:

$$\sigma = \sqrt{10\sigma_R^2 + k_D} = 1.733$$

Thus, in an exemplary instrument, the signal noise in a channel using n accumulations for a total of t seconds is:

$$\sigma = \sqrt{\sum_n 0.548^2 + 2.81 \cdot 10^{-3} t}$$

Integrating a signal over a number of m channels decreases the error by $1/\sqrt{m}$. The two cases, one from the hydrogen 585 line and the other the silane 2186 line, will be discussed below. Typically, 15 seconds of signal integration repeated over 5 accumulations is used. The camera noise integrated over m channels is $$\sigma/\sqrt{m} = \sqrt{\frac{5 \cdot 0.548^2 + 2.81 \cdot 10^{-3} \cdot 75}{m}}$$

For hydrogen m~183, and for silane m~1533. In these cases, the average noise is ~0.1 and ~0.033 counts, respectively, while typical signal counts at the inlet are 6.29E+05 and 5.63E+05 counts for hydrogen and silane, respectively. Therefore, the dark noise and read noise of the camera, removed by subtraction, are negligible.

The Raman signal (I) has an intrinsic noise that is exactly the square root of the total counts. The relative signal noise is:

$$\sigma_R = 1/\sqrt{I}$$

Typical relative errors are ~0.13% for hydrogen and silane, and ~1% for disilane.

Background Signal Noise and Resulting Error

The Raman signal is superimposed on a background signal due to the optical system from multiple causes. There is the Raman signal of the optical components, but more importantly, there is also a time-dependent fluorescent background from these same components. The time-dependent fluorescent background is minimized by bleaching the fluorescent impurities by prolonged exposure to the laser beam. This signal adds a curvature to the baseline that is time dependent, and prevents perfect baseline subtraction.

Figure 10:
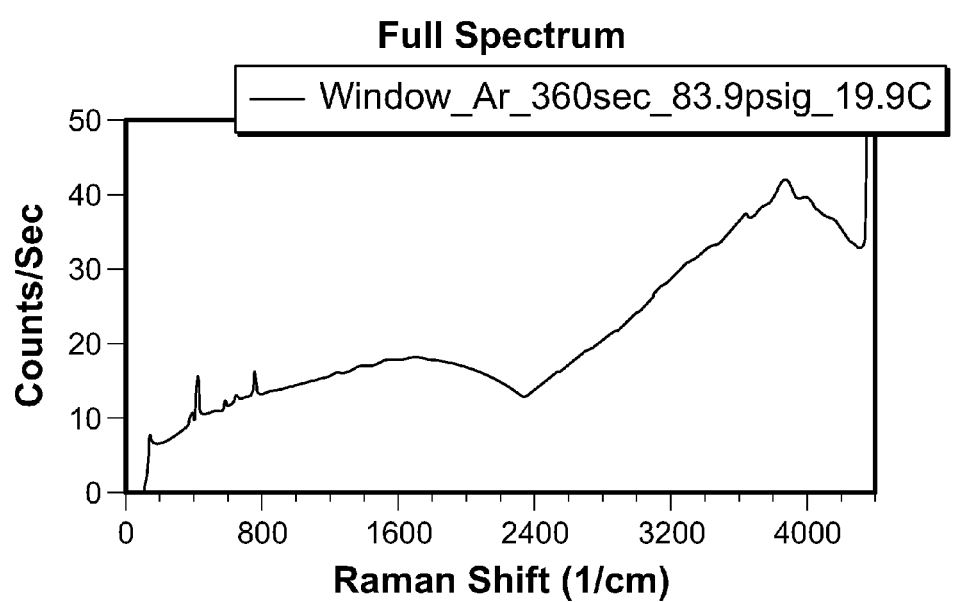
FIG. 10 is a graph plotting the full spectrum of an empty gas cell.

FIG. 10 shows an empty gas cell spectrum that is bleached. The inflection point is due to a join of spectral bands on the CCD detector, which is due to the optical system being equivalent do an echelle spectrograph+cross dispersing prism. The position of the join is to some extent selectable. The small sharp peaks to the left in FIG. 10 are window Raman peaks. These Raman peaks are very weak and do not overlap the hydrogen line with any significant intensity. Examination of the full data shows that in this instrument the best line for analytical work is the 586/cm line.

Figure 11:
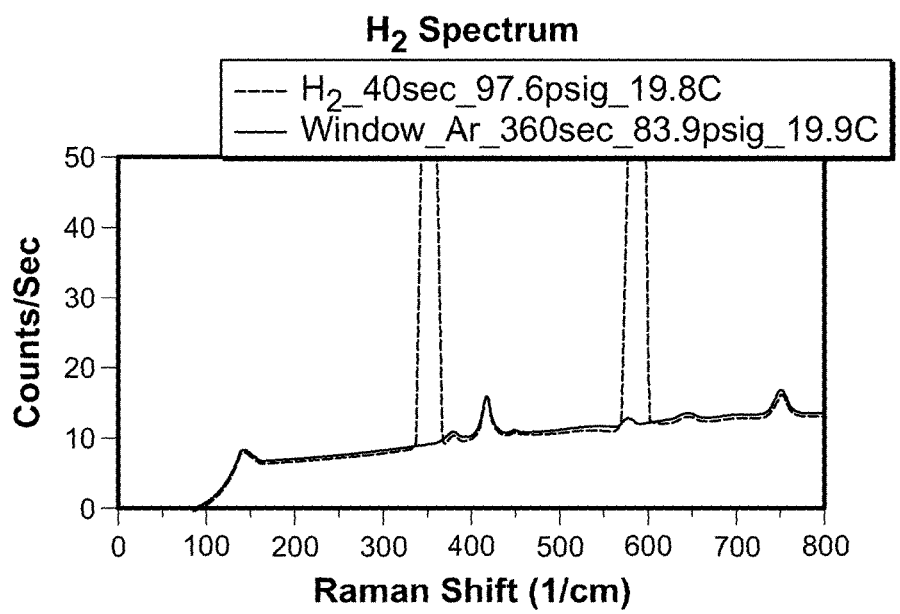
FIG. 11 is a graph plotting the Hydrogen ($H_2$) spectrum superimposed with window background.
Figure 12:
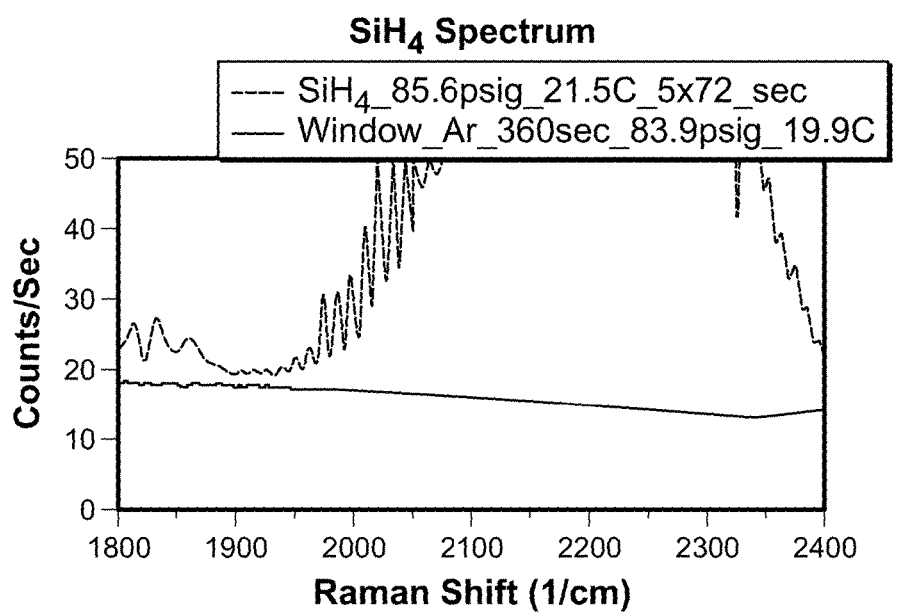
FIG. 12 is a graph plotting the silane ($SiH_4$) spectrum superimposed over a slightly curved fluorescent background.

Hydrogen ($H_2$) spectrum with window background superimposed is shown in FIG. 11. The 586 line is suitable for Hydrogen analytical work The 2186/cm silane band from 1930 to 2450/cm superimposed over a slightly curved fluorescent background is shown in FIG. 12.

Neglecting the curvature around hydrogen is perfectly valid and introduces negligible error. However, the error for silane signal integration must be considered.

Figure 13:
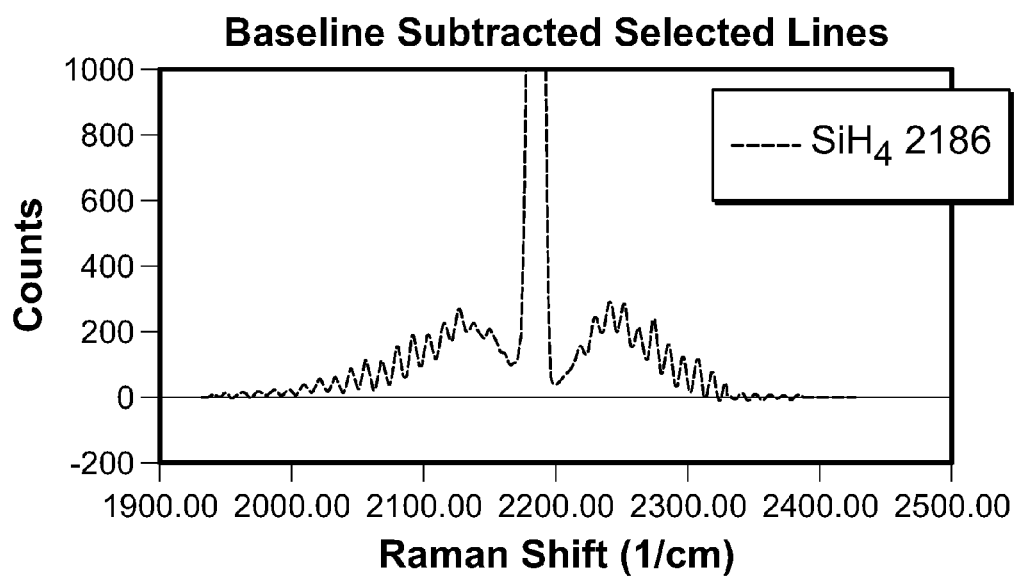
FIG. 13 is a graph plotting the silane ($SiH_4$) signal from an fluidized bed reactor experiment with simple, straight line baseline subtraction.
Figure 14:
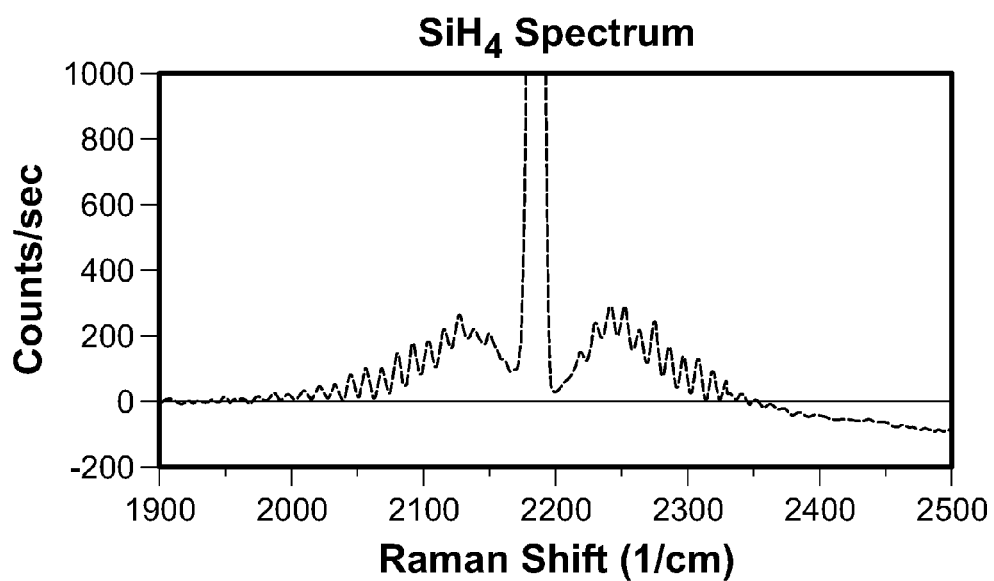
FIG. 14 is a graph plotting the silane ($SiH_4$) signal from an fluidized bed reactor experiment with simple, straight line baseline subtraction.

FIGS. 13 and 14 show a silane signal from the FBR experiment with simple, straight line baseline subtraction. The integrated area is 5.63E5 counts, as shown in FIG. 13. Subtracting the estimated background (linearly scaled), the integrated area is 5.88E5 counts, as shown in FIG. 14.

Neglect of the baseline curvature on average introduces a higher error of about +2% in $SiH_4$ concentration (12 data sets). The window background is linearly scaled such that the signal at 1930/cm is equal to the signal at 2350/cm. This is determined by the requirement that the signal should dip to zero at each ripple from the 2186 central line. The expected improvement in signal error, including intrinsic Raman noise, is reduced to approximately 0.5% by this procedure. For the hydrogen line, this procedure should not be applied, because the local fluorescent background is flat. The (local and very weak) window lines should not be amplified to the point that they are in interference.

Figure 15:
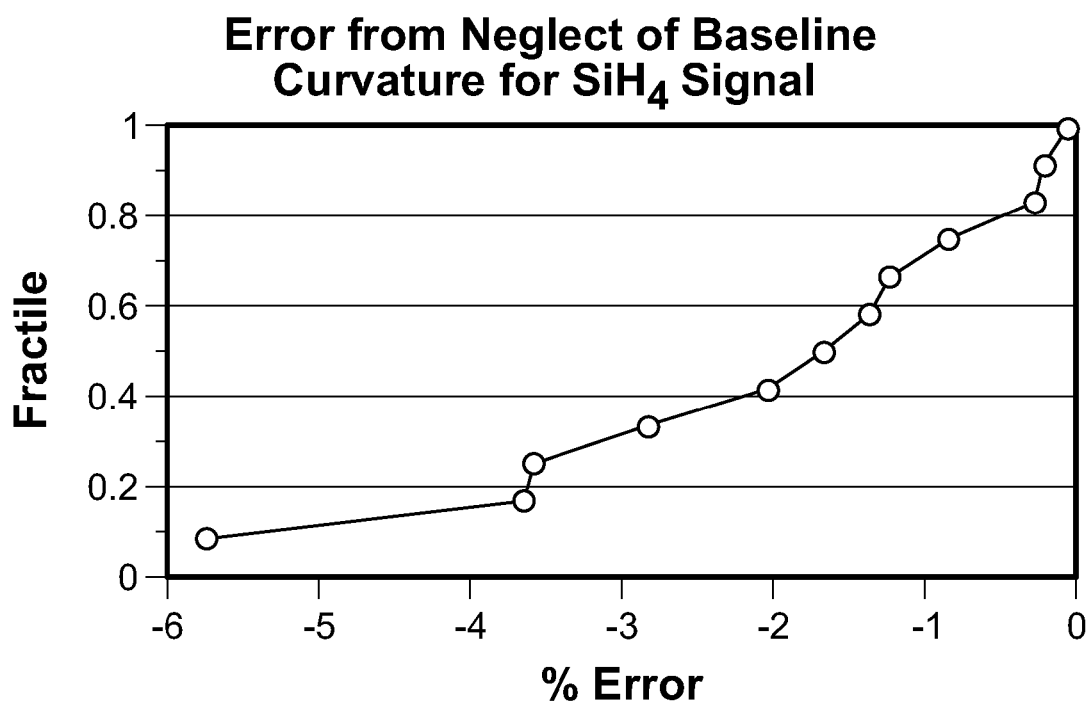
FIG. 15 is a graph plotting the error from neglect of baseline curvature for the silane ($SiH_4$) signal.

Neglect of baseline curvature introduces an error in the silane signal, as shown in FIG. 15. From this distribution, we see the error is systematic with a mean value of −2% with respect to the same data corrected for baseline curvature. The expected mean error when using curved baseline subtraction is ~0.44%.

Use of the above embodiments reduced the response time for silane analysis from approximately 6 minutes by chromatography to approximately 2 minutes, and detection of silicon oligomers, such as, for disilane ($Si_2H_6$) from approximately 20 minutes to approximately 2 minutes. Thus, the above embodiments provide a process control system that operates in real-time to simultaneously compute conversion efficiency to solid silicon and gas-by-products. Another advantage of the above embodiments is a reduced risk of an un-calibrated or drifting calibration control system.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions and methods without departing from the scope of the invention, it is intended that all matter contained in the above description and shown in the accompanying drawing[s] shall be interpreted as illustrative and not in a limiting sense. The method described herein is not limited by the particular process or reactor configuration disclosed herein. For example, the method may be applied to other configurations and processes related to the operation of a continuous fluidized bed reactor.

What is claimed is:

1. A method of operating a gas decomposition reactor having an inlet and an exhaust outlet, the method comprising:
    continuously measuring a chemical composition of an exhaust gas located within the exhaust outlet using Raman spectra and generating a corresponding exhaust signal, wherein at least two components of the exhaust gas are detected simultaneously;
    continuously measuring a chemical composition of an inlet gas located within the inlet using Raman spectra and generating a corresponding inlet signal;
    comparing the measured chemical composition of the exhaust gas to the measured chemical composition of the inlet gas to ratiometrically determine a conversion efficiency of a reaction in the gas decomposition reactor based at least in part on the inlet signal and the exhaust signal; and
    adjusting a flow of an inlet gas through the inlet based at least in part on the determined conversion efficiency to change a subsequently measured chemical composition of a subsequent exhaust gas located within the gas outlet.

2. The method of claim 1, wherein the chemical composition of the exhaust gas is measured by a Raman spectrometer.

3. The method of claim 2, wherein a processor is connected with the Raman spectrometer to receive a signal from the Raman spectrometer to compare the measured chemical composition of the exhaust gas to the measured chemical composition of the inlet gas.

4. The method of claim 1, wherein the flow of the inlet gas is adjusted by a pressure control system.

5. The method of claim 4, wherein the pressure control system is connected with the inlet gas for regulating the flow of the inlet gas through the inlet.

6. The method of claim 1, wherein the inlet gas comprises a first gas and a second gas and the chemical composition of the inlet gas is measured by a Raman spectrometer.

7. The method of claim 1, wherein the flow of the inlet gas through the inlet is adjusted in real time based at least in part on the determined conversion efficiency.

8. The method of claim 1, wherein a Raman spectrometer is connected with the inlet and the exhaust outlet through Raman probes for determining the chemical composition of the inlet gas and the exhaust gas.

9. The method of claim 1, wherein the inlet gas is a mixture of a first gas and a second gas.

10. The method of claim 9, wherein a flow of one of the first gas and the second gas is regulated by a pressure control system connected with one of the first gas and the second gas.

11. The method of claim 1, wherein the gas decomposition reactor is a fluidized bed reactor.

12. The method of claim 11, wherein the inlet gas is a mixture of a reaction gas and a fluidizing gas.

13. The method of claim 12, wherein a flow of the reaction gas and the flow of the fluidizing gas is regulated by a pressure control system separately connected with a source of the reaction gas and a source of the fluidizing gas.

14. The method of claim 12, wherein the reaction gas is silane and the fluidizing gas is hydrogen.

* * * * *